United States Patent [19]
Koé

[11] Patent Number: 5,914,786
[45] Date of Patent: Jun. 22, 1999

[54] DEVICE FOR MEASURING THE SURFACE OF PRINTED MATTER

[75] Inventor: Reginald Edgar Koé, Hollandscheveld, Netherlands

[73] Assignee: Grafisch Management Adviesbureau GMA. B.V., Hollandscheveld, Netherlands

[21] Appl. No.: 08/750,116

[22] PCT Filed: Apr. 1, 1996

[86] PCT No.: PCT/NL96/00138

§ 371 Date: Mar. 14, 1997

§ 102(e) Date: Mar. 14, 1997

[87] PCT Pub. No.: WO96/30743

PCT Pub. Date: Oct. 3, 1996

[30] Foreign Application Priority Data

Mar. 31, 1995 [NL] Netherlands ............................ 9500628

[51] Int. Cl.⁶ ........................................................ G01J 3/50
[52] U.S. Cl. ........................................ 356/446; 250/559.16
[58] Field of Search .................................... 356/445, 446, 356/447, 448; 250/559.16

[56] References Cited

U.S. PATENT DOCUMENTS

| | | | |
|---|---|---|---|
| 3,771,877 | 11/1973 | Rosencranz | 356/446 |
| 3,892,492 | 7/1975 | Eichenberger | 356/446 |
| 4,053,235 | 10/1977 | Hampton et al. | 356/446 |
| 5,198,875 | 3/1993 | Bazin et al. | 356/369 |
| 5,260,584 | 11/1993 | Popson et al. | 356/448 |
| 5,400,138 | 3/1995 | Peterson et al. | 356/402 |

FOREIGN PATENT DOCUMENTS

| | | |
|---|---|---|
| 0 299 445 | 1/1989 | European Pat. Off. . |
| 0 475 803 | 3/1992 | European Pat. Off. . |
| 88 16 390 | 8/1989 | Germany . |

*Primary Examiner*—Richard A. Rosenberger
*Attorney, Agent, or Firm*—Evenson, McKeown, Edwards & Lenahan P.L.L.C.

[57] ABSTRACT

The invention relates to a device for measuring properties of a printed surface. The device comprises a base provided with a viewer, a housing which is mounted on the base for pivoting on a pivot shaft and which is movable between an upward pivoted positioning situation and a downward pivoted measuring position. The device also comprises at least one sensor unit which is mounted in a position in the housing such that it is directed at the viewer in the measuring position. The device also comprises a processing device incorporated in the housing which receives signals from the sensor unit and processes these to measurement data, and an information display arranged on the housing for displaying a number of measurement data characters, wherein the pivot shaft extends substantially parallel to a transverse direction of the characters and to the side of the housing lying above the characters and the viewer is arranged on the side of the base lying beneath the characters.

15 Claims, 3 Drawing Sheets

DEVICE FOR MEASURING THE SURFACE OF PRINTED MATTER

The invention relates to a device for measuring properties of a printed surface. Such a device is for instance a densitometer with which the density of the printed image and/or of the separate basic colours can be measured.

Devices of this type comprise a viewer which is placed over the part of the surface for measuring. In known devices this viewer is situated on the side remote from the user, so that it is difficult to see and awkward to place over the printed surface for measuring. Known devices are generally provided with an information display on which the measured values are shown. When the user wishes to measure at a position somewhat removed from himself, the display is not sufficiently visible to enable reading of the measured values. For each measurement the user must then pick up the device in order to be able to look at the display.

Another drawback of the known devices is that an overall view of all important data cannot be obtained therewith. A separate measuring device must be used for each quantity to be measured.

The invention now has for its object to provide a device of the type stated in the preamble with which these drawbacks are obviated. This object is achieved with the device for measuring properties of a printed surface according to the invention characterized. Herein the viewer is situated on the side of the device facing toward the user, so that it can be seen very easily, even at a greater distance, and can be placed precisely on the surface part for measuring. Moving of the housing from the positioning situation into the measuring position takes place very comfortably with a single movement of the wrist.

In another embodiment of the present invention, the information display is arranged on the housing such that in the measuring position it extends at an angle of between 10° and 40D relative to a plane defined by the base and extends substantially parallel to the pivot shaft. Thus is achieved that when the housing is pivoted into the measuring position, the information display pivots into a osition very suitable for reading, so that this information display can be read properly even at a great distance. In this embodiment, the angle amounts substantially to 25°.

A further favorable development is characterized in claim 4. By placing the viewer on the protrusion it can be observed very well from different directions.

In another advantageous embodiment of the present invention, a number of control keys are arranged on the side of the information display lying above the characters. The control keys are hereby situated at a location very close to the fingers of the user when the latter is holding the device to position the viewer and pivot the housing from the positioning situation into the measuring position.

In the current embodiment, at least one of the control keys is a measurement type selection key with which the processing device can be switched into different processing modes for the measurement signals. Once the device has been positioned, i.e. the viewer has been placed on the surface for measuring, different measurements can be performed successively in simple manner by depressing the measurement type selection key. A very suitable embodiment is the processing modes comprise a density measurement of a printing plate and a density measurement of an image surface. The device can thereby be used in two different departments of a printing firm, i.e. the department where the printing plates are manufactured and the phototypesetting or lithographic reproduction department.

In a further embodiment of the present invention, the processing modes comprise a density measurement of a printed surface and a gloss measurement of the printed surface. In this embodiment, the sensor unit comprises a main sensor which is arranged straight above the viewer and a first light source which is directed at the viewer at an angle. The sensor unit further comprises a second light source and a gloss sensor in mutually opposing positions which are directed onto the viewer at an angle. Here, the main sensor, the first light source and the viewer define a first plane. Additionally, the main sensor, the gloss sensor, the second light source and the viewer lie in a second plane perpendicular to the first plane. Furthermore, between at least the main sensor and the viewer is arranged a polarization filter, the passage direction of which is parallel to the first plane. The polarization filter which is necessary to eliminate gloss for the density measurement does not impede the gloss measurement, since the reflections for measuring in the gloss measurement can pass through this filter, because the paths of the light rays for the gloss measurement lie in the plane rotated through 90■ relative to the plane of the paths of the light rays for the density measurement.

It is therefore possible to allow the polarization filter to intersect at least some of the connecting lines between the first and second light source and the gloss meter on the one hand and the viewer on the other, if this is desired for the construction or the operation of the device.

In yet another embodiment of the present invention, the main sensor comprises light sensors which are sensitive to respectively the basic colors and black/white. In one measurement the densities in the different basic colours can then for instance be measured or a balance measurement of these densities can be performed.

In the present embodiment, the gloss sensor comprises an array of sensors, the sensor elements of which lie in the second plane and which are each directed at the viewer, so that it becomes possible to measure the gloss at different angles in favorable manner, in order to gain an indication of whether or not the gloss has a diffuse character.

The invention will be further elucidated in the following description with reference to the annexed figures.

Figure 1:
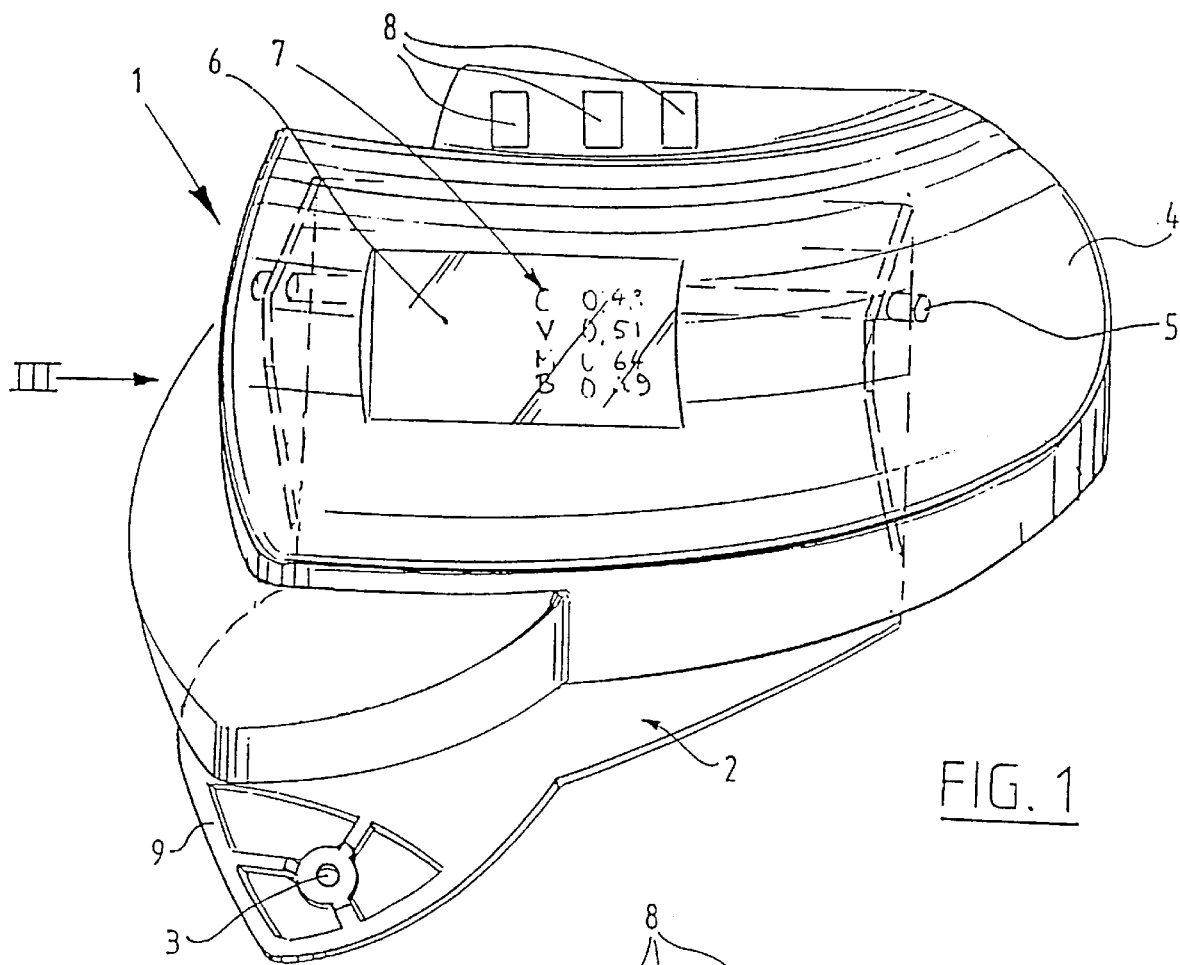
FIG. 1 shows a perspective view of a device according to a preferred embodiment of the invention in the positioning situation.
Figure 2:
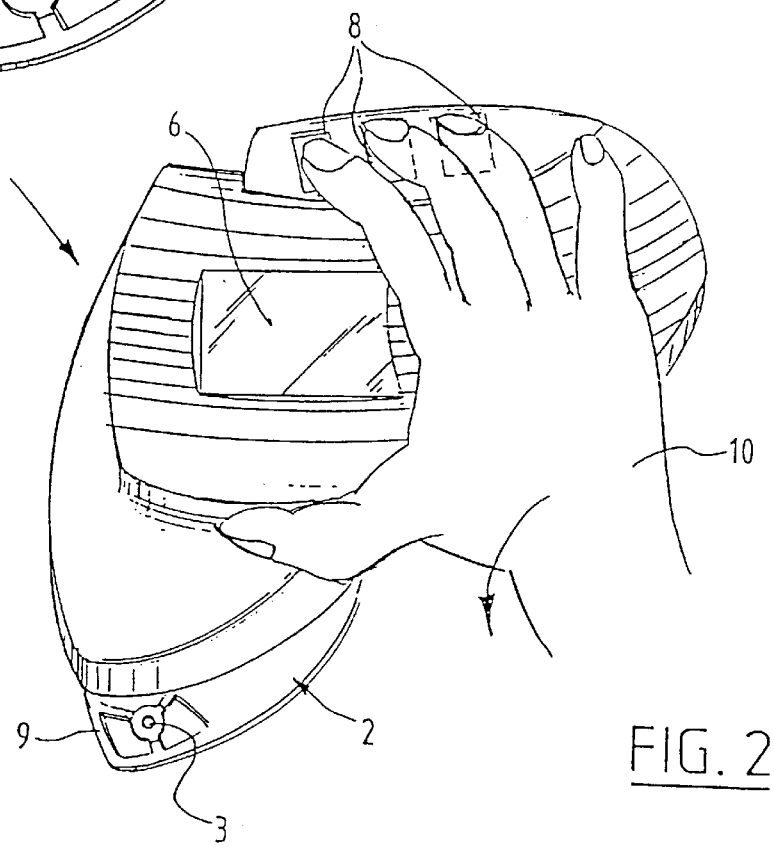
FIG. 2 shows the use of the device of FIG. 1.

The device 1 shown in FIG. 1 comprises a base 2 provided with a viewer 3. In order to measure the properties of the printed surface the device 1 is placed with its base 2 on the printed surface. care is herein taken that viewer 3 coincides with the surface part for measuring.

The device 1 further comprises a housing 4 pivotally connected on a pivot shaft 5 to the base 2. The housing 4 can be pivoted downward from the positioning situation shown in FIGS. 1 and 3, in which the viewer 3 is visible, into a measuring position shown in FIG. 4, in which a sensor unit 12 to be further described hereinbelow is accurately positioned above the viewer, in order to perform the measurement.

Incorporated in the device 1 is a processing unit (not shown) which processes the signals from the sensor unit 12 to measurement data. This measurement information is shown on an information display 6 arranged on housing 4 in the form of a number of measurement data characters 7.

As shown in the figures, the pivot shaft 5 extends substantially parallel to a transverse direction of the characters 7 and to the side of the housing lying above the characters 7.

Figure 3:
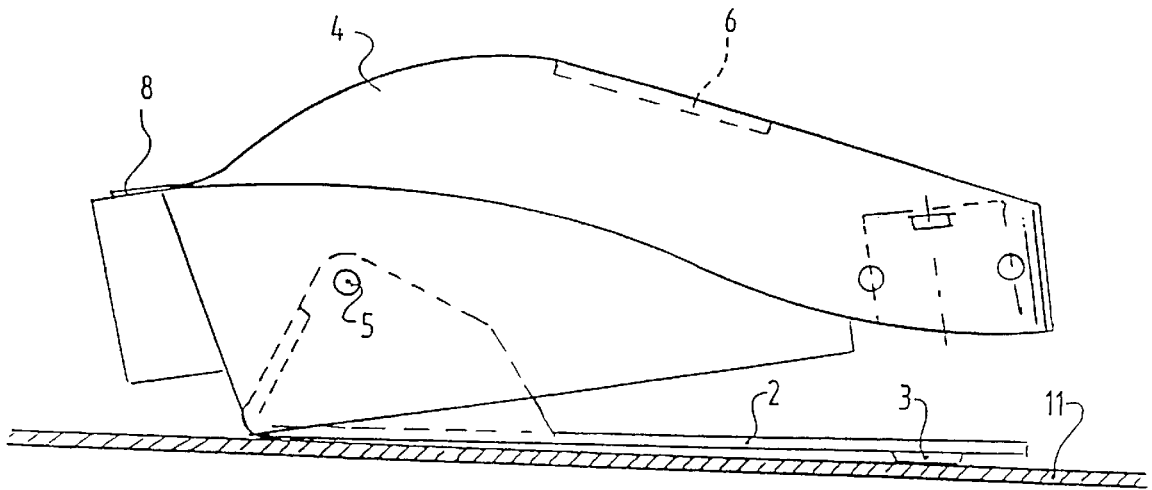
FIG. 3 shows a side view of the device of FIG. 1.
Figure 4:
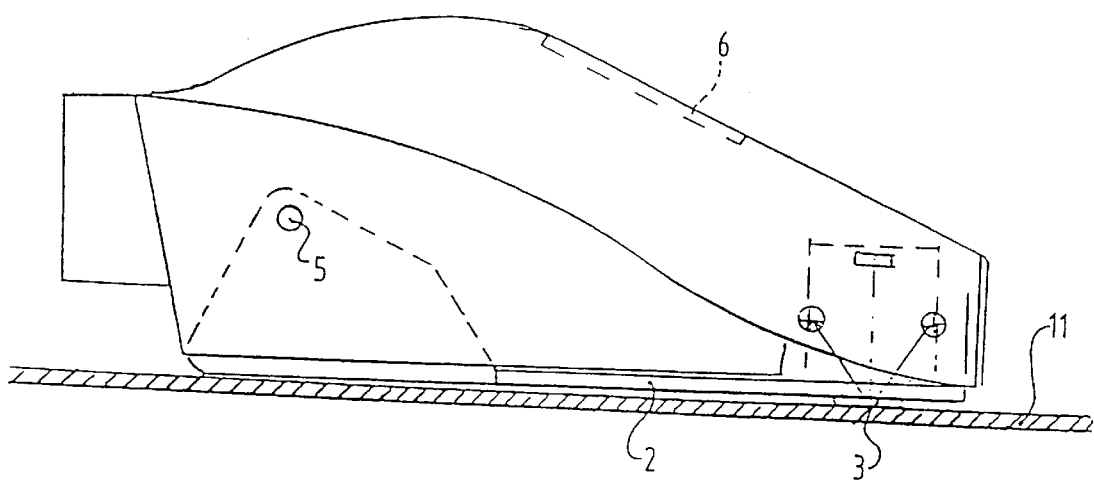
FIG. 4 shows a side view corresponding with FIG. 3 with the device in the measuring position.

It will be apparent in the side views of FIGS. 3 and 4 that the upper side of the characters is situated on the left and the lower side on the right. As shown in these side views, the pivot shaft 5 is thus situated on the top side of the characters and the viewer 3 on the bottom side thereof.

Due to this relative arrangement of the components of device 1 the user will be able to lay his hand 10 on the housing 4 of the device, wherein viewer 3 is situated on the side of the housing facing the user. This user thereby has a very good view of the viewer 3 and even at arm's length can still manoeuvre viewer 3 accurately above a place for measuring. When viewer 3 is positioned correctly, the user has only to press his hand 10 downward in order to cause housing 4 to pivot round pivot shaft 5 from the positioning situation to the measuring position.

As shown in FIGS. 3 and 4, the information display 6 is arranged on housing 4 such that in the measuring position shown in FIG. 4 it extends at an angle of about 25■ relative to the printed surface 11. The user hereby has a very good view of the display 6 and of the information characters 7 displayed therein, even when the measurement is performed at arm's length.

Formed on the device in the shown preferred embodiment is a protrusion 9 in which the viewer 3 is arranged. Viewer 3 can hereby be discerned particularly well. In the positioning situation there is a maximum space between the base and the housing at the position of the viewer 3, so that a good view of viewer 3 is obtained.

It is noted that the pivot shaft 5 does not have to be a continuous shaft, but can also be defined by two pivot points.

Arranged on housing 4 on the side of the housing lying above the characters is a number of control keys 8. These control keys can be operated by the user in very suitable manner since they are situated in the position where the user will let his fingers rest when holding the housing 4.

The keys 8 can be used for different purposes, although in the preferred embodiment shown here at least one of these keys 8 is a measurement type selection key with which the processing device can be switched into different processing modes for the measurement signals. The device according to the invention can be embodied for combining different types of measurement. A very suitable combination is for instance the density measurement of a printing plate and a density measurement of a printed surface. One of these types of measurement is chosen by activating control keys 8 in suitable manner. The density measurement can only be performed for black/white values but also, or instead, for the basic colours. In addition to a density measurement of the separate basic colours and/or black/white the processing device can for instance also determine and show in information display 6 a balance of the measured densities.

In the preferred embodiment shown in the figures the sensor unit, the processing unit and the information display are embodied such that both a density measurement and a gloss measurement can be performed. In a density measurement any gloss must be eliminated, while in a gloss measurement it is precisely the gloss which is decisive. To enable compliance with this conflicting condition, the sensor unit of device 1 is embodied in a special manner, which is shown schematically in FIG. 5.

Figure 5:
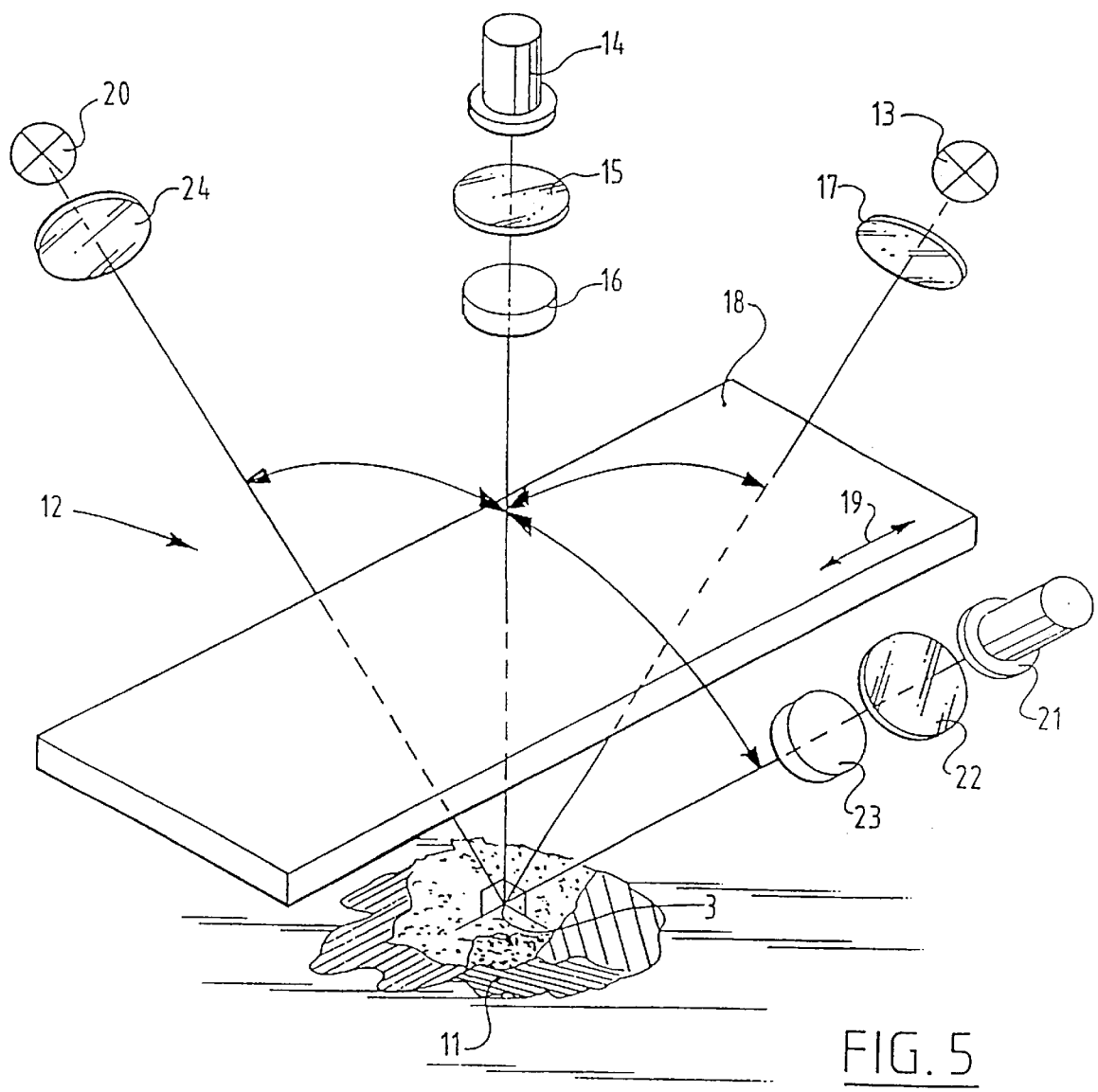
FIG. 5 shows schematically the sensor unit of the device.

Designated with 11 in FIG. 5 is the printed surface and with 3 the point of the printed surface which is being situated in the viewer and of which the densities and the gloss must be determined.

The sensor unit 12 comprises a main sensor 14 which is arranged straight above the point 3, and therefore straight above the viewer, and a first light source 13 which is directed at the viewer 3 at an angle.

A lens 17 provides focussing of the light from light source 13 onto the point 3 and a lens 16 provides focussing onto the main sensor 14 of the light reflected from the point 3. Further arranged in front of main sensor 14 is a filter 15 which filters out light components not visible to the human eye, so that the measured value from sensor 14 is indicative of the visible image.

The main sensor 14 is here shown as one element but can for instance comprise four light-sensitive cells which are each sensitive to respectively one of the basic colours (red, green and blue) and the whole spectrum.

The main sensor 14 is intended for measuring the densities in the measuring point 3. In order to prevent a measurement error due to gloss, a polarization filter 18 is arranged with a passage direction 19 coinciding with the plane through the first light source 13, viewer 3 and main sensor 14.

The measurement signals from main sensor 14, or from each of the elements thereof, are processed by the processing unit to measurement information which is shown in information display 6.

By operating one of the control keys 8 a gloss measurement can be performed instead of the density measurement described above. This is for instance done immediately following on from the density measurement.

For this gloss measurement the sensor unit 12 comprises a second light source 20 and a sensor 21, here referred to as a gloss sensor. The light source 20 and the gloss sensor 21 in mutually opposing positions are directed onto the viewer 3 at an angle so that the specular reflection of light source 20 in the measuring point 3 can be measured by gloss sensor 21. Here also a lens 24 is arranged in front of light source 20 in order to focus the light on the measuring point 3 and a lens 23 is arranged in front of gloss sensor 21 which focuses the reflected light onto gloss sensor 21. A filter 22 once again filters out the non-visible light components.

In order to measure the gloss value the measurement signal from gloss sensor 21 is corrected with the simultaneous measurement signal from main sensor 14. This latter measures the diffuse reflection of the light from light source 20. The result of the processing is the actual gloss value. This is again shown on the information display 6.

The polarization filter 18 is in any case arranged in the light path between measuring point 3 and main sensor 14. The filter 18 can however be arranged such that all light paths intersect the filter 18. Because light source 20 and gloss sensor 21 are arranged with main sensor 24 in a plane perpendicular to the plane through main sensor 14, viewer 3 and light source 13, the specular reflection will pass freely through filter 18.

Light sources 13 and 20 are preferably positioned at 45■. relative to the normal of the measurement plane, i.e. the line between main sensor 14 and measuring point 3. The gloss sensor 21 can be arranged at an angle of between 45 and 75■ relative to this normal. As noted above, gloss sensor 21 can also comprise an array of sensor elements which all lie in the plane defined by the light source, the measuring point 3 and the main sensor 14. With this array of sensors an indication can be obtained of the distribution of the angle at which the gloss is visible.

The device shown and described here is a preferred embodiment. The invention can be embodied in many different ways. The processing of the signals from the sensor unit 12 are per se known, so that there is no further discussion thereof in this description.

I claim:

1. Device for measuring properties of a printed surface comprising a base provided with a viewer, a housing which is mounted on the base for pivoting on a pivot shaft and which is movable between an upward pivoted positioning situation and a downward pivoted measuring position, at least one sensor unit which is mounted in a position in the housing such that it is directed at the viewer in the measuring position, a processing device incorporated in the housing which receives signals from the sensor unit and processes these to measurement data, and an information display arranged on the housing for displaying a number of measurement data characters;

wherein the pivot shaft extends substantially parallel to a transverse direction of the characters and to the side of the housing lying above the characters and the viewer is arranged on the side of the base lying beneath the characters and the viewer is formed on a protrusion extending to the left and downward relative to the characters.

2. Device as claimed in claim 1, wherein the information display is arranged on the housing such that in the measuring position it extends at an angle of between 10° and 40° relative to a plane defined by the base and extends substantially parallel to the pivot shaft.

3. Device as claimed in claim 2, wherein the angle amounts substantially to 25°.

4. Device as claimed in claim 2, wherein the viewer is formed on a protrusion extending to the left and downward relative to the characters.

5. Device as claimed in claim 2, wherein a number of control keys is arranged on the side of the information display lying above the characters.

6. Device as claimed in claim 1, wherein a number of control keys is arranged on the side of the information display lying above the characters.

7. Device as claimed in claim 6, wherein at least one of the control keys is a measurement type selection key with which the processing device can be switched into different processing modes for the measurement signals.

8. Device as claimed in claim 7, wherein the processing modes comprise a density measurement of a printing plate and a density measurement of an image surface.

9. Device as claimed in claim 7, wherein the processing modes comprise a density measurement of a printed surface and a gloss measurement of the printed surface.

10. Device as claimed in claim 9, wherein the sensor unit comprises a main sensor arranged straight above the viewer and a first light source which is directed at the viewer at an angle, a second light source and a gloss sensor in mutually opposing positions which are directed onto the viewer at an angle, wherein the main sensor, the first light source and the viewer define a first plane, and the main sensor, the gloss sensor, the second light source and the viewer lie in a second plane perpendicular to the first plane, and wherein between at least the main sensor and the viewer is arranged a polarization filter, the passage direction of which is parallel to the first plane.

11. Device as claimed in claim 10, wherein the polarization filter moreover intersects at least some of the connecting lines between the first and second light source and the gloss meter on the one hand and the viewer on the other.

12. Device as claimed in claim 11, wherein the main sensor comprises part-sensors which are sensitive to respectively the basic colours and black/white.

13. Device as claimed in claim 11, wherein the gloss sensor comprises an array of sensors, the sensor elements of which lie in the second plane and which are each directed at the viewer.

14. Device as claimed in claim 10, wherein the main sensor comprises light sensors which are sensitive to respectively the basic colors and black/white.

15. Device as claimed in claim 10, wherein the gloss sensor comprises an array of sensors, the sensor elements of which lie in the second plane and which are each directed at the viewer.

* * * * *